United States Patent
Akizuki et al.

(10) Patent No.: US 10,602,742 B2
(45) Date of Patent: *Mar. 31, 2020

(54) METHOD FOR CULTIVATING CORN OR SOYBEAN

(71) Applicant: Sumitomo Chemical Company, Limited, Tokyo (JP)

(72) Inventors: Naoya Akizuki, Kasai (JP); Atsushi Iwata, Walnut Creek, CA (US); Yasutaka Shimokawatoko, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/027,619

(22) PCT Filed: Oct. 17, 2013

(86) PCT No.: PCT/JP2013/078751
§ 371 (c)(1),
(2) Date: Apr. 6, 2016

(87) PCT Pub. No.: WO2015/056357
PCT Pub. Date: Apr. 23, 2015

(65) Prior Publication Data
US 2016/0249622 A1    Sep. 1, 2016

(51) Int. Cl.
| | |
|---|---|
| *A01N 57/20* | (2006.01) |
| *A01C 1/00* | (2006.01) |
| *A01N 51/00* | (2006.01) |
| *A01N 25/00* | (2006.01) |
| *A01N 47/40* | (2006.01) |
| *A01N 43/88* | (2006.01) |
| *A01N 43/50* | (2006.01) |

(52) U.S. Cl.
CPC ............... *A01N 57/20* (2013.01); *A01C 1/00* (2013.01); *A01N 25/00* (2013.01); *A01N 43/50* (2013.01); *A01N 43/88* (2013.01); *A01N 47/40* (2013.01); *A01N 51/00* (2013.01)

(58) Field of Classification Search
CPC combination set(s) only.
See application file for complete search history.

(56) References Cited

U.S. PATENT DOCUMENTS

| | | | |
|---|---|---|---|
| 2008/0161367 A1 | 7/2008 | Voeste et al. | |
| 2008/0261811 A1* | 10/2008 | Krohn | A01N 37/46 504/100 |
| 2011/0312493 A1* | 12/2011 | Oostendorp | A01N 57/20 504/128 |
| 2012/0015804 A1 | 1/2012 | Terada et al. | |

FOREIGN PATENT DOCUMENTS

| | | | | |
|---|---|---|---|---|
| JP | 2011057629 A | 3/2011 | | |
| WO | WO-2012039068 A1 * | 3/2012 | ............. | A01N 25/00 |

OTHER PUBLICATIONS

International Search Report dated Jan. 14, 2014 in International Application No. PCT/JP2013/078751.
International Preliminary Report on Patentability dated Apr. 19, 2016 in International Application No. PCT/JP2013/078751.
Office Action Brazilian Patent Application No. 112016008403-9 dated Jul. 25, 2019.

* cited by examiner

*Primary Examiner* — John Pak
*Assistant Examiner* — Daniel L Branson
(74) *Attorney, Agent, or Firm* — Panitch Schwarze Belisario & Nadel LLP; Lars H. Genieser; Megan E. Coyle

(57) ABSTRACT

A method is provided for cultivating soybean or corn. Also provided is a method for controlling insect pests in a field of soybean or corn. By these methods, insect pests in the fields of soybean or corn can be controlled. Therefore, a good yield of corn or soybean can been obtained.

4 Claims, No Drawings

METHOD FOR CULTIVATING CORN OR SOYBEAN

CROSS-REFERENCE TO RELATED APPLICATION

This application is a Section 371 of International Application No. PCT/JP2013/078751, filed Oct. 17, 2013, which was published in the English language on Apr. 23, 2015, under International Publication No. WO 2015/056357 A1, and the disclosure of which is incorporated herein by reference.

TECHNICAL FIELD

The present invention relates to a method for cultivating corn or soybean. Also, the present invention relates to a method for controlling insect pests in a field of soybean or corn.

BACKGROUND ART

Neonicotinoid compounds are known as active ingredients for insecticides. Metalayl compounds are known as active ingredients for fungicides. In addition, some organophosphorus compounds are also known as active ingredients for herbicides.

CITATION LIST

Non Patent Literature

Non-patent Document 1: Crop Protection Handbook, vol. 89 (2003)

SUMMARY OF INVENTION

Technical Problem

More efficient method for cultivating corn or soybean is desired.

Solution of Problem

The present invention provides a systematic method for cultivating corn or soybean which can obtain a good yield of corn or soybean. In the present invention, the good yield of corn or soybean can be obtained by controlling effect on pests including insect pests, plant pathogens and weeds by using a neonicotinoid compound, a metalaxyl compound and an organophosphorus compounds The present invention comprises treating soybean or corn seeds with at least one neonicotinoid compound and at least one metalaxyl compound, and after sowing the soybean or corn seeds in the field, treating the field with at least one organophosphorus compound. As a result, excellent control effects on insect pests occurring in the field can be exhibited.

The present invention relates to the followings.

[1] A method for cultivating soybean or corn, comprising a step of sowing a field with seeds of soybean or corn wherein a resistance to an inhibitor of 5-enolpyruvylshikimate-3-phosphate synthase or an inhibitor of glutamine synthase are imparted to the soybean or corn and the seeds are treated with at least one neonicotinoid compound selected from the group consisting of clothianidin, thiamethoxam and imidacloprid, and at least one metalaxyl compound selected from the group consisting of metalaxyl and metalaxyl-M, and then a step of treating the field with at least one organophosphorus compound selected from the group consisting of glyphosate, glufosinate, glufosinate-P, and agriculturally acceptable salts of these compounds.

[2] The method according to item [1], wherein the at least one neonicotinoid compound is clothianidin.

[3] The method according to item [2], wherein the step of sowing a field with seeds of soybean or corn is the step of sowing a field with seeds of soybean.

[4] The method according to item [3], wherein one or more beneficial characteristics are imparted to the soybean.

[5] The method according to item [2], wherein the step of sowing a field with seeds of soybean or corn is the step of sowing a field with seeds of corn.

[6] The method according to item [5], wherein one or more beneficial characteristics are imparted to the corn.

[7] A method for controlling insect pests in a field of soybean or corn, comprising the steps of:
a step of treating soybean or corn seeds wherein a resistance to an inhibitor of 5-enolpyruvylshikimate-3-phosphate synthase or an inhibitor of glutamine synthase are imparted to the soybean or corn with at least one neonicotinoid compound selected from the group consisting of clothianidin, thiamethoxam and imidacloprid, and at least one metalaxyl compound selected from the group consisting of metalaxyl and metalaxyl-M,
a step of sowing a field with seeds treated, and then,
a step of treating the field with at least one organophosphorus compound selected from the group consisting of glyphosate, glufosinate, glufosinate-P, and agriculturally acceptable salts of these compounds.

Effect of Invention

According to the present invention, controlling effect on pests, especially on insects in the corn field or soybean field, can be obtained, as a result, a good yield of corn or soybean can be obtained.

DESCRIPTION OF EMBODIMENTS

The method for cultivationg soybean or corn according to the present invention includes the steps of:

(1-1) a step of sowing a field with seeds of soybean or corn wherein a resistance to an inhibitor of 5-enolpyruvylshikimate-3-phosphate synthase or an inhibitor of glutamine synthase are imparted to the soybean or corn and the seeds are treated with at least one neonicotinoid compound selected from the group consisting of clothianidin, thiamethoxam and imidacloprid, and at least one metalaxyl compound selected from the group consisting of metalaxyl and metalaxyl-M, and then (1-2) a step of treating the field with at least one organophosphorus compound selected from the group consisting of glyphosate, glufosinate, glufosinate-P, and agriculturally acceptable salts of these compounds.

The method for controlling insect pests according to the present invention includes the steps of:

(2-1) a step of treating soybean or corn seeds wherein a resistance to an inhibitor of 5-enolpyruvylshikimate-3-phosphate synthase or an inhibitor of glutamine synthase are imparted to the soybean or corn with at least one neonicotinoid compound selected from the group consisting of clothianidin, thiamethoxam and imidacloprid, and at least one metalaxyl compound selected from the group consisting of metalaxyl and metalaxyl-M, (2-2) a step of sowing a field with seeds treated, and then, (2-3) a step of treating the field with at least one organophosphorus compound selected from the group consisting of glyphosate, glufosinate, glufosinate-P, and agriculturally acceptable salts of these compounds.

The step of sowing a field with soybean or corn seeds treated with at least one neonicotinoid compound selected from the group consisting of clothianidin, thiamethoxam and imidacloprid, and at least one metalaxyl compound selected from the group consisting of metalaxyl and metalaxyl-M (Above-mentioned (1-1); (2-1) and (2-2)).

In the present invention, the soybean seeds and the corn seeds are those wherein a resistance to an inhibitor of 5-enolpyruvylshikimate-3-phosphate synthase (e.g. glyphosate) or an inhibitor of glutamine synthase (e.g. glufosinate) are imparted to the soybean or corn. The examples of such glyphosate resistant soybean and corn cultivars include Roundup Ready (registered trademark), Agrisure GT, and the like. Similarly, the examples of such glufosinate resistant soybean and corn cultivars include LibertyLink (registered trademark), and the like.

In the present invention, one or more beneficial characteristics can be imparted to the soybean seeds and the corn seeds by a classical breeding method, a genetic engineering technique or the like. Examples of the beneficial characteristic may be a resistance to at least one herbicide such as an inhibitor of 4-hydroxyphenylpyruvic acid dioxygenase (hereinafter referred to as HPPD) (e.g. isoxaflutole), an inhibitor of acetolactate synthase (hereinafter referred to as ALS)(e.g. imazethapyr, thifensulfuron-methyl), an auxin type herbicide (e.g. 2,4-D, dicamba), bromoxynil, and the like. The example of such cultivars include Optimum GAT (registered trademark) which are resistant to both glyphosate and ALS inhibitors and the like.

The resistance to a herbicide imparted by a classical breeding method include the resistance to an imidazolinone type ALS inhibitor herbicide (e.g. imazethapyr), sulfonylurea type ALS inhibitor herbicide such as thifensulfuron-methyl, acetyl CoA carboxylase inhibitor such as a trione oxime or aryloxyphenoxypropionic acid herbicide, and the like. Crop plants to which resistance to an acetyl CoA carboxylase inhibitor has been imparted are described in Proc. Natl. Acad. Sci. USA (1990), 87, 7175-7179.

Mutant acetyl CoA carboxylase which is resistant to an acetyl CoA carboxylase inhibitor has been reported in Weed Science (2005) vol. 53, pp. 728-746, and a crop plant having resistance to an acetyl CoA carboxylase inhibitor can be produced when a gene encoding the mutant acetyl CoA carboxylase is introduced into a crop plant by a genetic engineering technique or when a mutation related to impartation of resistance is introduced into a gene encoding acetyl CoA carboxylase of a crop plant. Further, nucleic acids for introduction of a base substitution mutation can be introduced into cells of a crop plant by chimeraplasty (Gura T. 1999, Repairing the Genome's Spelling Mistakes, Science 285: 316-318) to induce a site-directed amino acid substitution mutation in the gene of acetyl CoA carboxylase or the ALS gene of the crop plant, whereby a crop plant resistant to an acetyl CoA carboxylase inhibitor or an ALS inhibitor can be produced.

A soybean crop plant resistant to dicamba can be produced by introducing a gene of dicamba-degrading enzyme such as dicamba monooxygenase isolated from *Pseudomonas maltophilia* into the plant (Behrens et. al. 2007 Dicamba Resistance: Enlarging and Preserving Biotechnology-Based Weed Management Strategies, Science 316: 1185-1188).

A crop plant resistant to both to a phenoxy acid herbicide (e.g. 2,4-D, MCPA, dichlorprop, or mecoprop) and an aryloxyphenoxypropionic acid herbicide (e.g. quizalofop, haloxyfop, fluazifop, dichlorfop, fenoxaprop, metamifop, cyhalofop, or clodinafop) can be produced by introducing a gene encoding an aryloxyalkanoate dioxygenase (WO 2005/107437, WO 2007/053482, WO 2008/141154).

A crop plant resistant to HPPD inhibitors can be produced by introducing a gene encoding HPPD which shows resistance to HPPD inhibitors (US2004/0058427).

Moreover, a crop plant resistant to herbicides can be produced by introducing genes described in WO98/20144, WO2002/46387, and US2005/0246800.

Examples of the beneficial characteristic may be an ability to produce an insecticidal protein by a genetic engineering technique. Examples of the insecticidal proteins produced by such a genetically engineered crop plant include insecticidal proteins;[delta]-endotoxins derived from *Bacillus cereus* and *Bacillus popilliae* (e.g. Cry1Ab, Cry1Ac, Cry1F, Cry1Fa2, Cry2Ab, Cry3A, Cry3Bb1 and Cry9C); and insecticidal proteins derived from Bacillus thuringiensis (e.g. VIP 1, VIP 2, VIP 3 and VIP 3A); insecticidal proteins derived from nematodes; toxins produced by animals, such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, luffin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl synthase; chitinase; and glucanase; and the like. The examples of such cultivars include Herculex I (registered trademark) (a corn cultivar expressing Cry1Fa2 toxin and phosphinothricin N-acetyltransferase (PAT) for imparting resistance to glufosinate).

In addition, the insecticidal toxin which is expressed in such a genetically engineered crop plant also includes hybrid toxins of [delta]-endotoxin proteins such as Cry1Ab, Cry1Ac, Cry1F, Cry1Fa2, Cry2Ab, Cry3A, Cry3Bb1, Cry9C, Cry34Ab and Cry35Ab, and insecticidal proteins such as VIP 1, VIP 2, VIP 3 and VIP 3A, and toxins in which a part is deleted or modified. The hybrid toxin is made by newly combining different domains of the insecticidal proteins with use of a genetic engineering technique. Cry1Ab in which a part of an amino acid sequence is deleted is known as an example of such a toxin in which a part is deleted. An example of the toxin in which a part is modified is a toxin in which one or more of amino acids of a naturally occurring toxin are substituted. The insecticidal toxin and the genetically engineered crop plant having an ability to synthesize the insecticidal toxin are described in EP-A-0374753, WO 93/07278, WO 95/34656, EP-A-0427529, EP-A-451878, WO03/052073, and the like. Such a toxin contained in these genetically engineered crop plants imparts to a plant resistance particularly to a coleopteran pest, a dipteran pest or a lepidopteran pest.

Moreover, genetically engineered crop plants which have one or more pest-resistant genes and thereby express one or more insecticidal toxins are also known.

Examples of the beneficial characteristic may be an aphid resistance by introducing, for example, the Rag 1 (Resistance Aphid Gene 1) gene.

Examples of the beneficial characteristic may be an ability to produce an anti-pathogen substance having a selective action by a genetic engineering technique. The known examples of such anti-pathogen substances are PR proteins (PRPs described in EP-A-0392225), and the like. These anti-pathogen substances and genetically engineered crop plants which produce such anti-pathogen substances are described in EP-A-0392225, WO 95/33818, EP-A-0353191, and the like. Examples of the anti-pathogen substances expressed in the genetically engineered crop plants include ion channel inhibitors such as sodium channel inhibitors and calcium channel inhibitors (KP1, KP4, KP6 toxins produced by viruses are known); stilbene synthase; bibenzyl synthase; chitinase; glucanase; PR proteins; and anti-pathogen substances produced by microorganisms, such as peptide antibiotics, heterocycle-containing antibiotics, and protein factors involved in plant disease-resistance (referred to as plant disease resistance genes and described in WO 03/000906).

Examples of the beneficial characteristic may be a modified oil component or an enhanced amino acid content by a genetic engineering technique. Examples of such beneficial characteristics include low linolenic soybean which has a reduced content of linolenic acid), and high-lysine (high-oil) corn (corn which has an increased content of lysine or oil).

Furthermore, the above-described crop plants include stacked plants which have a combination of two or more of the beneficial characteristics such as the above-described classical herbicide-resistant characteristic, or a herbicide-resistance gene, an insecticidal pest-resistance gene, an anti-pathogen substance-producing gene, a modified oil component, and an enhanced amino acid content.

The neonicotinoid compound of the present invention includes clothianidin, thiamethoxam, and imidacloprid, preferably clothianidin, and the metalaxyl compound of the present invention includes metalaxyl and metalaxyl-M.

The soybean or corn seeds treated with the neonicotinoid compound and the metalaxyl compound posses the neonicotinoid compound and the metalaxyl compound in the range of 0.001 to 40 g per 1 kg of seeds, preferably 0.005 to 10 g per 1 kg of seeds, respectively.

Soybean seeds or corn seeds treated with the neonicotinoid compound and the metalaxyl compound can be obtained by treating the neonicotinoid compound and a metalaxyl compound to soybean seed or corn seeds. The neonicotinoid compound and the metalaxyl compound are usually mixed with a solid carrier or a liquid carrier, formulated with optional addition of an auxiliary agent for formulation, such as surfactants, respectively and then the resultants are used for the treating soybean or corn seeds. Also, the mixture of the neonicotinoid compound and and the metalaxyl compound is mixed with a solid carrier or a liquid carrier, formulated with optional addition of an auxiliary agent for formulation, such as surfactants, respectively and then the resultant is used for the treating soybean or corn seeds.

The dosage of the neonicotinoid compound and the metalaxyl compound used for treating soybean or corn seeds are usually in the range of 0.001 to 40 g per 1 kg of seeds, preferably 0.005 to 10 g per 1 kg of seeds, respectively. The method for applying one or more active ingredients to plant seeds includes, for example, a method of subjecting a seed to dust coating with a formulation containing one or more active ingredients, a method of immersing a seed in a formulation containing one or more active ingredients, and a method of coating a seed with a carrier containing one or more active ingredients.

The neonicotinoid compound and metalaxyl compound can be treated on a seed independently or at the same time. Moreover, additionally one or more active ingredient can be treated on the seed independently or together with neonicotinoid compound and/or metalaxyl compound.

The step of treating the field with at least one organophosphorus compound selected from the group consisting of glyphosate, glufosinate, glufosinate-P, and agriculturally acceptable salts of these compounds.
(Above-Mentioned (1-2); (2-3)

The organophosphorus compound of the present invention includes glyphosate, glufosinate, glufosinate-P, and agriculturally acceptable salts of these compounds. Glyphosate, glufosinate, glufosinate-P, and agriculturally acceptable salts of these compounds are compounds described in The Pesticide Manual Fifteenth Edition (published by British Crop Production Council), page 587-589, 589-593 respectively, and can be prepared by known processes; said compounds or formulations thereof are commercially available. The agriculturally acceptable salts of glyphosate mean salts such as ammonium salt, diammonium salt, trimesium salt, isopropylamine salt, sodium salt, potassium salt, guanidine salt and the like, of glyphosate. The agriculturally acceptable salts of glufosinate mean salts such as ammonium salt and the like, of glufosinate. The agriculturally acceptable salts of glufosinate-P mean salts such as sodium salt and the like, of glufosinate-P.

In the step of treating a field with the organophosphorus compound, such an organophosphorus compound is usually mixed with a solid carrier or a liquid carrier, formulated with optional addition of an auxiliary agent for formulation, such as surfactants, and then used.

The organophosphorus compound is treated with the field of corn field or soybean field.

The dosage of the organophosphorus compound used for treating the field is usually 100 to 5000 g per 10,000 m$^2$ preferably 200 to 3000 g per 10,000 m$^2$. In the step of treating the field with the organophosphorus compound, an adjuvant may be mixed at the time of such treatment with the organophosphorus compound.

In the case where the organophosphorus compound is applied after sowing soybean seeds, the organophosphorus compound is applied from emergence to throughout flowering.

In the case where the organophosphorus compound is applied after sowing corn seeds, the organophosphorus compound is applied from emergence through the V8 stage (8 leaves with collars) or until corn height reaches 30 inches.

According to the method for controlling insect pests of the present invention, insect pests in the fields of soybean or corn can be controlled.

Examples of such insect pests include the followings.

Coleopteran pest such as *Cerotoma trifurcate, Myochrous Chaetocnema pulicaria, Chaetocnema ectypa, Agonoderus pallipes, Sphenophorus callosus, Diabrotica virgifera zeae, Diabrotica barberi, Diabrotica undecimpunctata howardi, Diabrotica virgifera virgifera, Limonius* spp., *Agrioted* spp., *Melanotus* spp., *Horistonotus* spp., *Sphenophorus maidis, Nicentrus testaceipes, Sitora lineatus, Colaspis brunnea, Euetheola rugiceps, philophaga* spp., *Amphimallon* sp., *Rhizotrogus* sp., *Cotinis* spp. , *Polyphylia* spp., *Lachnosterna farcta, Amphimallon* spp., *Popillia japonica*, and the like.

Dipteran pests such as *Delia platura*, and the like.

Hemipteran pests such as *Stictocephala festina, Blissus leucopterus, Rhopalosiphum maidis, Aphis glycines, Rhopalosiphum padi, Aulacorthum solani, Nezara viridula, Blissus leucopterus*, and the like.

Hymenopteran pests such as *Solenopsis saevissima*, and the like.

Lepidopteran pests such as *Agrotis segetum* and the like.
Thysanopteran pests such as *Frankliniella occidentalis*, *Frankliniella williamsi*, and the like.

In the method for controlling insect pests according to the present invention, one or more other agricultural chemicals may be used in combination. Such other agricultural chemicals include, for example, insecticides, acaricides, nematicides, fungicides, herbicides, plant growth regulators, and safeners.

EXAMPLES

The present invention will be illustrated by the following examples, but the present invention is not limited to these examples. In addition, "ha" in the following descriptions means hectare, i.e. 10,000 m².

First of all, evaluation criteria for an insecticidal effect described in the following examples are shown.

[Insecticidal Effect]

The evaluation of the insecticidal effect is performed by determining the life and death of the insects at the time of the investigation and calculating the protective value according to the following equation;

Protective Value (%)=100×(1−T/C)

wherein the symbols have the following meanings;

C: The number of insects at the time of observation in an untreated section; and T: The number of insects at the time of observation in a treated section.

Example 1

Clothianidin, at the rate of 1.0 g par 1 kg seed and metalaxyl, at the rate of 0.6 g par 1 kg seed are applied to herbicide tolerant soybean (registered trademark: Roundup Ready Soybean) seeds. Then, soil is packed in a pot, and above seeds are sown. The pot is placed in a greenhouse. 18 days after sowing, *Aulacorthum solani* are placed on the soybean leaf. 19 days after sowing, glyphosate-isopropylamine is uniformly applied to the soybean at the rate of 1,200 g par ha.

21 days after sowing, the pesticidal effect against *Aulacorthum solani* is examined. As a result, a control effect against the *Aulacorthum solani* can be confirmed.

Example 2

Clothianidin, at the rate of 0.5 g par 1 kg seed and metalaxyl-M, at the rate of 0.04 g par 1 kg seed are applied to herbicide tolerant soybean (registered trademark: Liberty Link Soybean) seeds. Then, soil is packed in a pot, and above seeds are sown. The pot is placed in a greenhouse. 18 days after sowing, *Aulacorthum solani* are placed on the soybean leaf. 19 days after sowing, glufosinate-ammonium is uniformly applied to the soybean at the rate of 500 g par ha.

21 days after sowing, the pesticidal effect against *Aulacorthum solani* is examined. As a result, a control effect against the *Aulacorthum solani* can be confirmed.

Example 3

Clothianidin, at the rate of 4.0 g par 1 kg seed and metalaxyl, at the rate of 0.15 g par 1 kg seed are applied to herbicide tolerant corn (registered trademark: Liberty Link Corn) seeds. Then, soil is packed in a pot, and above seeds are sown. The pot is placed in a greenhouse. 18 days after sowing, *Rhopalosiphum padi* are placed on the corn leaf. 19 days after sowing, glufosinate-ammonium is uniformly applied to the corn at the rate of 500 g par ha.

21 days after sowing, the pesticidal effect against *Rhopalosiphum padi* is examined. As a result, a control effect against the *Rhopalosiphum padi* can be confirmed.

Example 4

Clothianidin, at the rate of 1.0 g par 1 kg seed and metalaxyl-M, at the rate of 0.04 g par 1 kg seed are applied to herbicide tolerant corn (registered trademark: Roundup Ready Corn) seeds. Then, soil is packed in a pot, and above seeds are sown. The pot is placed in a greenhouse. 18 days after sowing, *Rhopalosiphum padi* are placed on the corn leaf. 19 days after sowing, glyphosate-isopropylamine is uniformly applied to the corn at the rate of 1,200 g par ha.

21 days after sowing, the pesticidal effect against *Rhopalosiphum padi* is examined. As a result, a control effect against the *Rhopalosiphum padi* can be confirmed.

Example 5

Thiamethoxam, at the rate of 0.5 g par 1 kg seed and metalaxyl, at the rate of 0.15 g par 1 kg seed are applied to herbicide tolerant soybean (registered trademark: Roundup Ready Soybean) seeds. Then, soil is packed in a pot, and above seeds are sown. The pot is placed in a greenhouse. 18 days after sowing, *Aulacorthum solani* are placed on the soybean leaf. 19 days after sowing, glyphosate-isopropylamine is uniformly applied to the soybean at the rate of 1,200 g par ha.

21 days after sowing, the pesticidal effect against *Aulacorthum solani* is examined. As a result, a control effect against the *Aulacorthum solani* can be confirmed.

Example 6

Thiamethoxam, at the rate of 1.0 g par 1 kg seed and metalaxyl-M, at the rate of 0.3 g par 1 kg seed are applied to herbicide tolerant soybean (registered trademark: Liberty Link Soybean) seeds. Then, soil is packed in a pot, and above seeds are sown. The pot is placed in a greenhouse. 18 days after sowing, *Aulacorthum solani* are placed on the soybean leaf. 19 days after sowing, glufosinate-ammonium is uniformly applied to the soybean at the rate of 500 g par ha.

21 days after sowing, the pesticidal effect against *Aulacorthum solani* is examined. As a result, a control effect against the *Aulacorthum solani* can be confirmed.

Example 7

Thiamethoxam at the rate of 1.0 g par 1 kg seed and metalaxyl, at the rate of 0.6 g par 1 kg seed are applied to herbicide tolerant corn (registered trademark: Liberty Link Corn) seeds. Then, soil is packed in a pot, and above seeds are sown. The pot is placed in a greenhouse. 18 days after sowing, *Rhopalosiphum padi* are placed on the corn leaf. 19 days after sowing, glufosinate-ammonium is uniformly applied to the corn at the rate of 500 g par ha.

21 days after sowing, the pesticidal effect against *Rhopalosiphum padi* is examined. As a result, a control effect against the *Rhopalosiphum padi* can be confirmed.

Example 8

Thiamethoxam, at the rate of 10 g par 1 kg seed and metalaxyl-M, at the rate of 0.01 g par 1 kg seed are applied to herbicide tolerant corn (registered trademark: Roundup Ready Corn) seeds. Then, soil is packed in a pot, and above seeds are sown. The pot is placed in a greenhouse. 18 days after sowing, *Rhopalosiphum padi* are placed on the corn leaf. 19 days after sowing, glyphosate-isopropylamine is uniformly applied to the corn at the rate of 1,200 g par ha.

21 days after sowing, the pesticidal effect against *Rhopalosiphum padi* is examined. As a result, a control effect against the *Rhopalosiphum padi* can be confirmed.

Example 9

Imidacloprid, at the rate of 2.3 g par 1 kg seed and metalaxyl, at the rate of 0.6 g par 1 kg seed are applied to herbicide tolerant soybean (registered trademark: Roundup Ready Soybean) seeds. Then, soil is packed in a pot, and above seeds are sown. The pot is placed in a greenhouse. 18 days after sowing, *Aulacorthum solani* are placed on the soybean leaf. 19 days after sowing, glyphosate-isopropylamine is uniformly applied to the soybean at the rate of 1,200 g par ha.

21 days after sowing, the pesticidal effect against *Aulacorthum solani* is examined. As a result, a control effect against the *Aulacorthum solani* can be confirmed.

Example 10

Imidacloprid, at the rate of 0.6 g par 1 kg seed and metalaxyl-M, at the rate of 0.04 g par 1 kg seed are applied to herbicide tolerant soybean (registered trademark: Liberty Link Soybean) seeds. Then, soil is packed in a pot, and above seeds are sown. The pot is placed in a greenhouse. 18 days after sowing, *Aulacorthum solani* are placed on the soybean leaf. 19 days after sowing, glufosinate-ammonium is uniformly applied to the soybean at the rate of 500 g par ha.

21 days after sowing, the pesticidal effect against *Aulacorthum solani* is examined. As a result, a control effect against the *Aulacorthum solani* can be confirmed.

Example 11

Imidacloprid, at the rate of 0.6 g par 1 kg seed and metalaxyl, at the rate of 0.15 g par 1 kg seed are applied to herbicide tolerant corn (registered trademark: Liberty Link Corn) seeds. Then, soil is packed in a pot, and above seeds are sown. The pot is placed in a greenhouse. 18 days after sowing, *Rhopalosiphum padi* are placed on the corn leaf. 19 days after sowing, glufosinate-ammonium is uniformly applied to the corn at the rate of 500 g par ha.

21 days after sowing, the pesticidal effect against *Rhopalosiphum padi* is examined. As a result, a control effect against the *Rhopalosiphum padi* can be confirmed.

Example 12

Imidacloprid, at the rate of 10 g par 1 kg seed and metalaxyl-M, at the rate of 0.04 g par 1 kg seed are applied to herbicide tolerant corn (registered trademark: Roundup Ready Corn) seeds. Then, soil is packed in a pot, and above seeds are sown. The pot is placed in a greenhouse. 18 days after sowing, *Rhopalosiphum padi* are placed on the corn leaf. 19 days after sowing, glyphosate-isopropylamine is uniformly applied to the corn at the rate of 1,200 g par ha.

21 days after sowing, the pesticidal effect against *Rhopalosiphum padi* is examined. As a result, a control effect against the *Rhopalosiphum padi* can be confirmed.

INDUSTRIAL APPLICABILITY

Insect pests in the fields of soybean or corn can be controlled by the method for controlling insect pests according to the present invention, therefore, a good yield of corn or soybean can been obtained.

The invention claimed is:

1. A method for cultivating soybean comprising:
   a step of sowing a field with seeds of soybean wherein a resistance to an inhibitor of glutamine synthase has been imparted to the seeds of soybean and wherein the seeds have been treated with clothianidin and at least one metalaxyl compound selected from the group consisting of metalaxyl and metalaxyl-M, and then
   a step of treating the field with at least one organophosphorus compound selected from the group consisting of glufosinate, glufosinate-P, and agriculturally acceptable salts of these compounds.

2. The method according to claim 1, wherein one or more beneficial characteristics have been imparted to the seeds of soybean.

3. A method for cultivating corn comprising:
   a step of sowing a field with seeds of corn wherein a resistance to an inhibitor of 5-enolpyruvylshikimate-3-phosphate synthase has been imparted to the seeds of corn and wherein the seeds have been treated with clothianidin and at least one metalaxyl compound selected from the group consisting of metalaxyl and metalaxyl-M, and then
   a step of treating the field with at least one organophosphorus compound selected from the group consisting of glyphosate, and agriculturally acceptable salts of this compound.

4. The method according to claim 3, wherein one or more beneficial characteristics have been imparted to the seeds of corn.

* * * * *